United States Patent [19]
Gomringer

[11] Patent Number: 5,376,077
[45] Date of Patent: Dec. 27, 1994

[54] INTRODUCER SHEATH WITH SEAL PROTECTOR

[75] Inventor: Gary R. Gomringer, La Mesa, Calif.

[73] Assignee: Interventional Technologies, Inc., San Diego, Calif.

[21] Appl. No.: 985,293

[22] Filed: Dec. 4, 1992

[51] Int. Cl.⁵ .......................................... A61M 5/178
[52] U.S. Cl. .................................................. 604/167
[58] Field of Search ............... 604/164, 167, 256, 283, 604/905

[56] References Cited

U.S. PATENT DOCUMENTS

| | | | |
|---|---|---|---|
| 1,180,665 | 4/1916 | McElroy . | |
| 2,229,739 | 12/1941 | Harrington | 128/272 |
| 2,818,864 | 1/1958 | Hudson | 128/272 |
| 4,133,441 | 1/1979 | Mittleman et al. | 215/247 |
| 4,535,818 | 8/1985 | Duncan et al. | 137/846 |
| 4,535,819 | 8/1985 | Atkinson et al. | 137/846 |
| 4,804,960 | 2/1989 | Kamen | 604/250 |
| 5,053,013 | 10/1991 | Ensminger et al. | 604/167 |
| 5,156,596 | 10/1992 | Balbierz et al. | 604/167 X |

FOREIGN PATENT DOCUMENTS

WO89/06553 7/1989 WIPO ................. A61M 37/00

*Primary Examiner*—Gene Mancene
*Assistant Examiner*—Thomas Price
*Attorney, Agent, or Firm*—Nydegger & Associates

[57] ABSTRACT

A device for introducing a rotatable atherectomy catheter into an artery of a patient comprises an elongated hollow introducer sheath attached to the distal end of a housing formed with a bore in which is mounted a seal. The seal is formed with an expandable opening to selectively prevent fluid flow through the seal. The seal includes a plurality of penetrable disks serially mounted in the bore. A permutation of slits and holes in the disks provides an assembled relationship allowing penetration of the seal by a catheter, while also preventing fluid leakage from the seal. The device includes a seal expander and a rear connector. The seal expander is engageable with the housing attached to the sheath, and the connector is engageable with the expander. The expander provides an insertion tube for penetrating the seal which expands to form a fluid tight seal around the insertion tube. The connector provides a second seal for preventing fluid leakage from the connector during operation of the rotatable catheter.

18 Claims, 4 Drawing Sheets

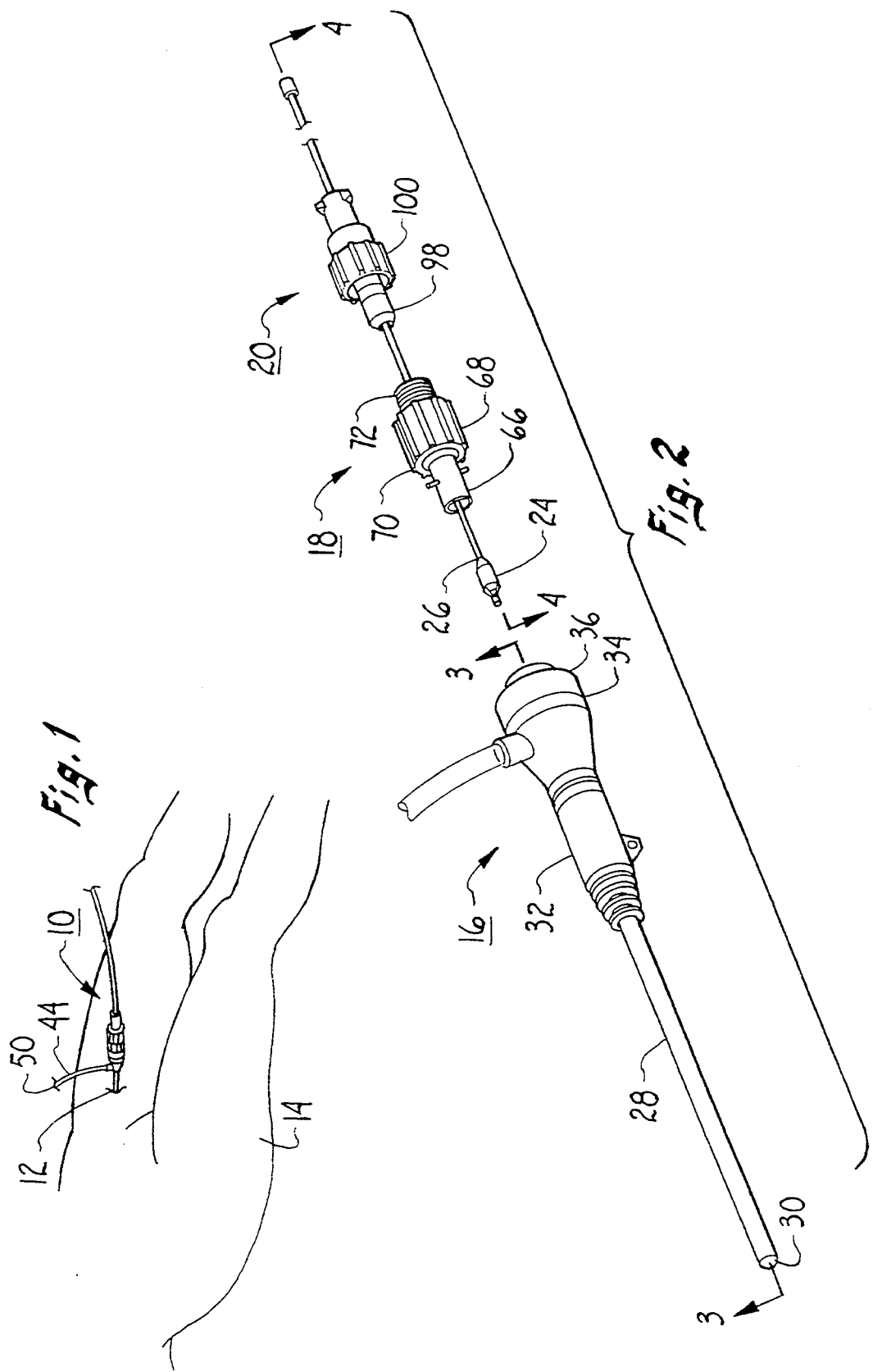

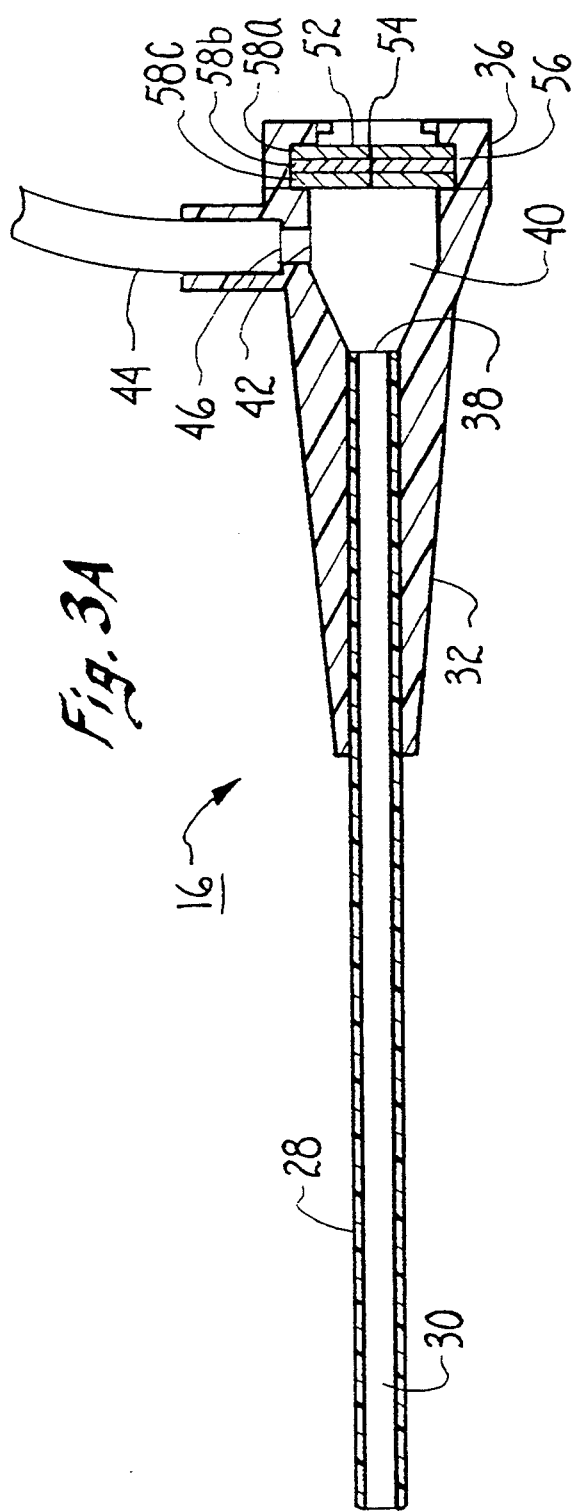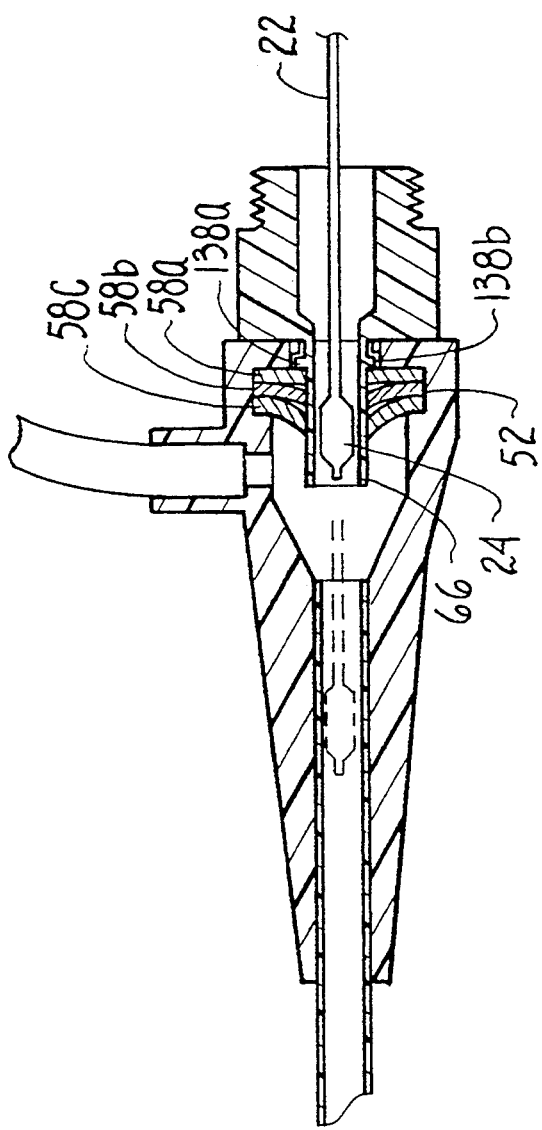

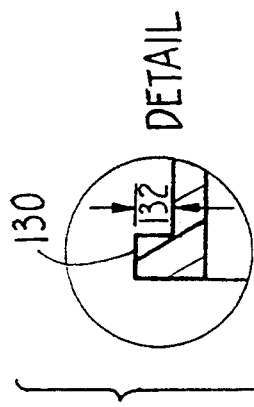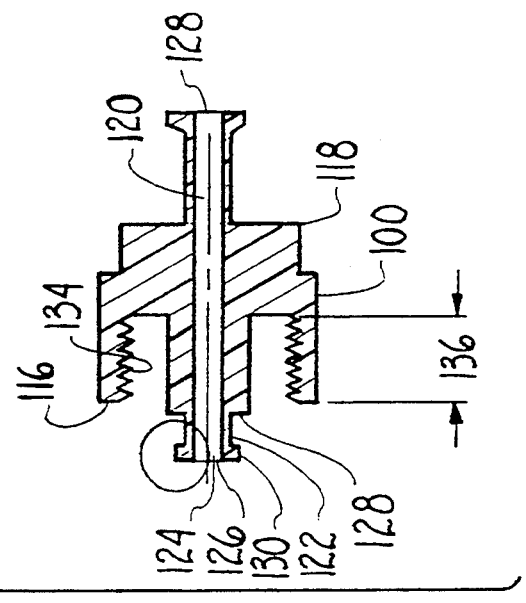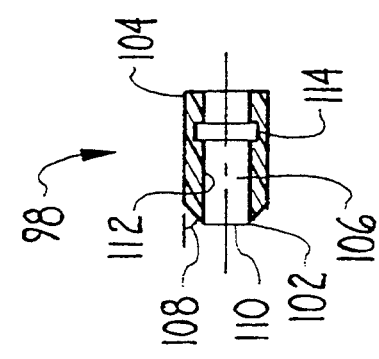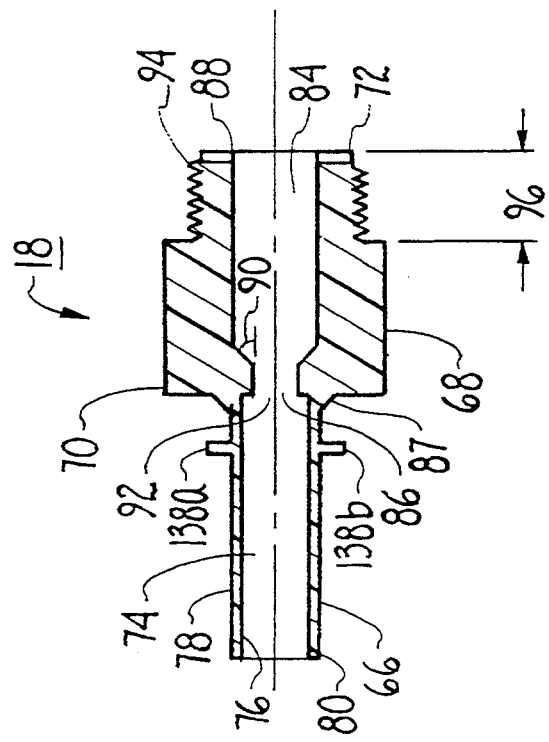

INTRODUCER SHEATH WITH SEAL PROTECTOR

TECHNICAL FIELD

The present invention generally pertains to apparatus for introducing a rotatable atherectomy device into an artery of a patient. More specifically, the present invention pertains to devices for allowing fluid access to the vessel of a patient while also providing access to the vessel of the patient by a rotatable atherectomy catheter. The present invention is particularly, but not exclusively, useful for preventing fluid leakage from the vessel of a patient during operation of a rotatable atherectomy catheter in the vessel of a patient.

BACKGROUND OF THE INVENTION

It is well known that achieving a fluid-tight seal is vital in a wide variety of situations. In the surgical environment, particularly in connection with surgical procedures requiring percutaneous entry into a vessel of a patient to remove stenotic blockages or plaque in an artery or other vessel of a patient, preventing fluid loss or leakage is essential. Whether in surgical or other environments, the permutations of problems associated with preventing fluid leakage are numerous.

Several examples occur in the field of atherectomy surgery. Atherectomy surgery was developed to avoid the problems of conventional bypass surgical procedures. Conventional bypass surgical techniques are extremely invasive. Atherectomy surgery is much less invasive. Atherectomy surgical techniques employ small cutting tools attached to a catheter. The atherectomy device can be inserted into the vessel of a patient through a less invasive incision in the patient, an incision not located near the heart. The cutting tool may be advanced until contact is made with a stenotic blockage in the vessel. When positioned at the stenosis, the cutting tool may be activated from outside the incision to cut away stenotic blockages. Atherectomy procedures, while extremely beneficial, have inherent fluid leakage problems.

One significant leakage problem results from the need to activate the catheter to rotate the cutting tool through the stenosis to remove the blockage. The catheter, typically inserted into the vessel of a patient through an introducer sheath, may extend a considerable distance from the distal tip of the cutting tool to the proximal end of the catheter, the proximal end being engaged with a device for rotating the catheter. Depending on the velocity of rotation of the catheter, the catheter may rotate both concentrically and eccentrically around the longitudinal axis of the catheter. A seal is needed to insure that fluids from the vessel of the patient do not leak from the introducer sheath during concentric and eccentric rotation of the catheter during a surgical routine.

Another of the leakage problems associated with atherectomy surgery arises from the need to change catheters during a surgical procedure. It may be necessary to change catheters and the cutting tool attached to the catheter. The problem to be solved is to remove the catheter from the vessel of the patient without inducing leakage through the introducer sheath. The concomitant problem is to be able to reinsert the atherectomy device through the introducer sheath without causing leakage from the vessel of the patient.

An additional potential leakage problem arises because of the cutting tool itself. As indicated, it may be necessary to insert and remove the catheter and cutting tool frequently during an atherectomy surgical procedure. Frequent contact between the blades of the cutting tool and a conventional introducer sheath seal ultimately will reduce effectiveness of the conventional seal. The solution is to provide a device for avoiding contact between the seal and the cutting tool during insertion and removal of the catheter.

Yet another related problem arises in connection with insertion of the cutting tool through an introducer sheath. The cutting tool itself could be dulled or damaged because of resistive pressure applied against the cutting tool by the seal during insertion of the catheter. Resiliency of the seal is not the solution. A seal which is too resilient may compromise the primary purpose of the seal, to prevent fluid leakage. The solution is to provide a device which permits insertion and removal of the cutting tool while avoiding contact between the cutting tool and the seal.

In light of the above, it is an object of the present invention to provide a device for introducing a rotatable atherectomy catheter into an artery of a patient. Another object of the present invention is to provide a seal which prevents fluid leakage during operation of a rotating catheter in the artery of a patient. Yet another object of the present invention is to provide a device for preventing leakage from the vessel of a patient during insertion and removal of a catheter during an atherectomy surgical process. An additional object of the present invention is to provide a device which precludes damage to the seal and to the cutting tool during insertion and removal of the catheter. Still another object of the present invention is to provide a device for introducing a rotatable atherectomy catheter into an artery of a patient which is easy to operate, is relatively easy to manufacture, and is comparatively cost effective.

SUMMARY OF THE INVENTION

A device for introducing a rotatable atherectomy catheter into an artery of a patient includes an elongated hollow sheath formed with a lumen. One end of the sheath is insertable into an artery or other vessel of a patient. The other end, which is attached to a cylindrically shaped housing, remains outside the body of the patient. The housing is formed with a bore for fluid communication with the lumen of the sheath.

The present invention also includes a seal formed with an expandable opening. The seal is mounted in the bore of the housing of the sheath. Preferably, the seal includes a plurality of penetrable disks of elastomeric material serially mounted in the bore of the housing. The object of the seal is to prevent fluid leakage from the sheath during insertion, operation and withdrawal of a rotatable atherectomy catheter which is inserted through the sheath into the vessel of a patient.

In the preferred embodiment of the present invention, the seal includes three separate disks. Specifically, there is a first disk having a circular hole in the center of the disk, a third disk having a radial slit through the center, and a second disk intermediate the first and third disks also having a radial slit through the center of the disk. The slit in the second disk is aligned substantially at right angles to the slit in the third disk. This configuration of the expandable seal allows penetration of the seal during insertion of a catheter. The configuration of the expandable seal also prevents fluid leakage from the seal during insertion, operation, and removal of the catheter during an atherectomy surgical procedure.

The rotatable atherectomy catheter is not inserted directly through the seal. Rather, the present invention includes a seal expander and a rear connector to penetrate the expandable seal. The seal expander is formed with a substantially cylindrical insertion tube which is attached to the body of the expander to form a first passageway. The insertion tube is insertable through the hole in the first disk, and subsequently through the slits in the second and third disks. The disks which comprise the seal grip the sides of the insertion tube to prevent fluid leakage from the lumen in the sheath. The seal expander is lockably engagable with the housing of the sheath. Engaging the housing of the sheath with the seal expander helps prevent fluid leakage from the first passageway.

The insertion tube fulfills another function. A rotatable catheter, with a cutting tools attached to the distal end, is insertable through the rear connector and through the seal expander prior to insertion of the catheter into a vessel of the patient through the sheath. The insertion tube surrounds the cutting tool attached to the rotatable catheter. Thus, the insertion tube, not the cutting tool, penetrates the seal. Consequently, the blades of the cutting tool cannot cut or abrade the seal during insertion or withdrawal of the catheter.

However, when the seal is parted by the insertion tube, the insertion tube is in fluid communication with the lumen of the sheath. A second passageway is formed in the seal expander, immediately proximal from the first passageway. The distal end of the second passageway is beveled. The seal expander is engagable with the rear connector. The rear connector is formed with a substantially cylindrical member. A second substantially tube shaped seal is attached to the cylindrical member. The second seal is tapered at the distal end. The tapering of the second seal forms an orifice at the distal end of the second seal. The orifice is circumferentially substantially the same diameter as that of the rotatable atherectomy catheter. When the seal expander and the rear connector are engaged, the tapered portion of the second seal is compressed by the beveled portion of the second passageway. The compressed second seal grips the circumference of the rotatable catheter during rotation of the catheter to prevent fluid leakage through the rear connector.

The novel features of this invention, as well as the invention itself, will best be understood from the accompanying drawings, taken together with the accompanying description in which similar reference characters refer to similar parts, and in which:

BRIEF DESCRIPTION OF THE DRAWINGS

FIG. 1 is a perspective view of the present invention operatively positioned in the femoral artery of a patient;

FIG. 2 is a perspective view of the device showing a rotatable atherectomy catheter, with a cutting tool attached, inserted through the seal expander and the rear connector of the present invention;

FIG. 3A is a cross-sectional view of the sheath and housing seen along the line 3—3 in FIG. 2;

FIG. 3B is a cross-sectional view of the sheath and housing seen along the line 3—3 in FIG. 2 after engagement of the seal expander and catheter with the housing;

FIG. 4A is a cross-sectional view of the seal expander seen along the line 4—4 in FIG. 2, without the atherectomy catheter inserted therethrough;

FIG. 4B is a cross-sectional view of the second seal, which during operation is attached to the rear connector, as seen along the line 4—4 in FIG. 2, without the atherectomy catheter inserted therethrough;

FIG. 4C is a cross-sectional view of the rear connector with the second seal unattached as seen along the line 4—4 in FIG. 2, without the atherectomy catheter inserted therethrough;

DESCRIPTION OF PREFERRED EMBODIMENTS

Figure 4D:
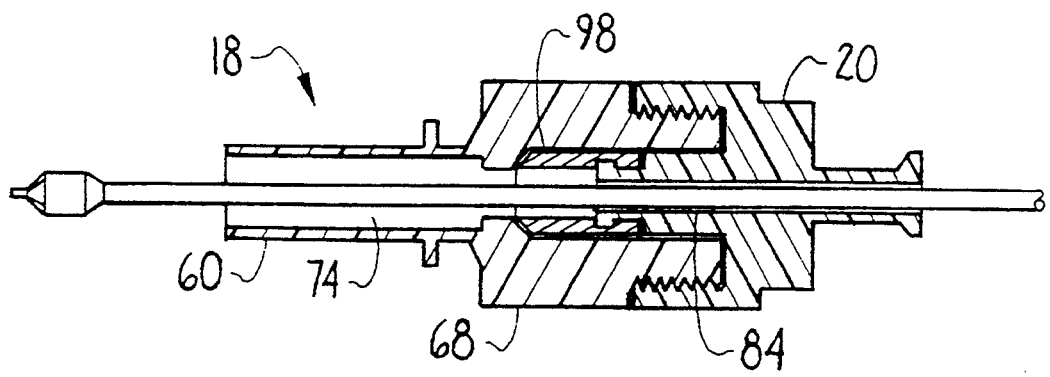
FIG. 4D is a cross-sectional view of the seal expander engaged with the rear connector as seen along the line 4—4 in FIG. 2 without the atherectomy catheter inserted therethrough.

Referring initially to FIG. 1, a device according to the present invention for introducing a rotatable atherectomy catheter into an artery of a patient is shown and generally designated 10. As shown, device 10 is operatively positioned in an entry site 12 of a patient 14 to perform any of a variety of surgical procedures employing a rotatable atherectomy catheter.

FIG. 2 is a perspective view of three major subassemblies of device 10 showing an introducer 16, a seal expander 18, and a rear connector 20. FIG. 2 further shows in the exploded perspective view the cooperation of device 10 with a rotatable atherectomy catheter 22 inserted through rear connector 20 and through seal expander 18. FIG. 2 also shows a cutting tool 24 attached to the distal end 26 of catheter 22.

FIG. 2 additionally shows that introducer 16 includes an elongated hollow sheath 28, formed with a lumen 30. Sheath 28 is attached to a housing 32 having a proximal end 34. A retaining ring 36 is attached to proximal end 34 of housing 32. To better appreciate the construction of introducer 16, FIG. 3A shows the proximal end 38 of sheath 28 is attached to housing 32 which is formed with a bore 40. A fluid port 42 is formed in bore 40 for fluid communication with lumen 30. An indeterminate length of flexible tubing 44, made of any flexible material well known in the art, is shown with an end 46 inserted in fluid port 42. The other end 48 of tubing 44 is attached to a valve 50, as shown in FIG. 1, to selectively control fluid communication through fluid port 42.

FIG. 3A further shows that introducer 16 also includes a seal 52 formed with an expandable opening 54. The actual construction of seal 54 is shown in FIG. 3A to include a plurality of elastomeric disks 56. For purposes of the present invention, the preferred embodiment of seal 52 includes a first disk 58a, a second disk 58b, and a third disk 58c serially mounted in bore 40 of housing 32 substantially perpendicular to a longitudinal axis through lumen 30 and bore 40. Disks 58a, 58b, and 58c are restrained in bore 40 by retaining ring 36.

Figure 5A:
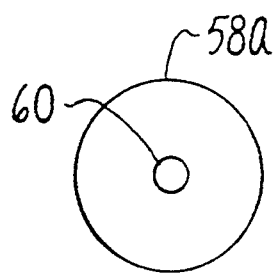
FIGS. 5A, 5B, and 5C are plan views of three disks comprising the seal when unparted by the rotatable atherectomy catheter.
Figure 5D:
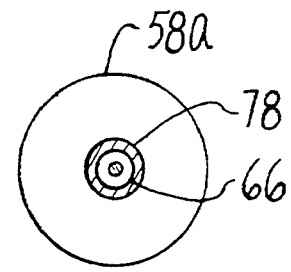
FIGS. 5D, 5E, and 5F are plan views of the three disks comprising the seal when parted by the insertion tube of the seal expander and a rotatable atherectomy catheter upon insertion of the catheter through the device.
Figure 5B:
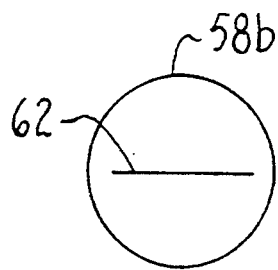
Figure 5E:
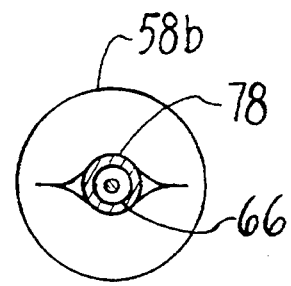
Figure 5C:
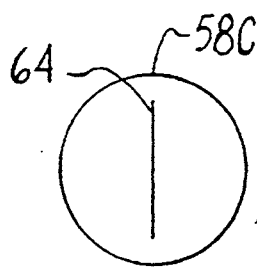

Referring now to FIG. 5A, it will be seen that first disk 58a is formed with a circular hole 60 through the center of first disk 58a. FIG. 5B shows that second disk 58b is formed with a first radial slit 62 through second disk 58b. FIG. 5C shows that third disk 58c is formed with a second radial slit 64 through third disk 58c. In the preferred embodiment of the present invention, radial slit 62 and radial slit 64 are aligned at substantially right angles when first disk 58a and second disk 58c and third disk 58c are mounted in bore 40 as shown in FIG. 3A.

Referring again to FIG. 2, it will be seen that seal expander 18 includes a substantially cylindrical insertion tube 66 attached to a cylindrical body 68 having a distal end 70 and a proximal end 72. The actual construction of seal expander 18 will best be appreciated by referring to FIG. 4A which shows insertion tube 66 is formed with first passageway 74 having an inner surface 76 and an outer surface 78. FIG. 4A also shows that insertion tube 66 has a distal end 80 and a proximal end 82. FIG. 4A additionally shows that body 68 is formed with a second passageway 84 having a distal end 86 and a proximal end 88. FIG. 4A also shows that proximal end 82 of insertion tube 66 is attached to distal end 70 of body 68 with first passageway 74 in alignment with second passageway 84. FIG. 4A further shows distal end 86 of second passageway 84 is beveled at an angle 90 to form a circular opening 92 between proximal end 82 of insertion tube 66 and distal end 70 of body 68. FIG. 4A also shows a first annular threaded surface 94 formed around body 68 a first threaded distance 96 from proximal end 72 of body 68 for lockably engaging rear connector 20 with seal expander 18.

Referring again to FIG. 2, it will be seen that rear connector 20 includes a tube shaped second seal 98 attached to a substantially cylindrical member 100. To better explain the construction of second seal 98, FIG. 4B shows second seal 98, disengaged from member 100, having and distal end 102 and a proximal end 104. FIG. 4B also shows second seal 98 is formed with a chamber 106. FIG. 4B further shows distal end 102 of second seal 98 is tapered to form an angle 108 which in turn forms an orifice 110 at distal end 102 of second seal 98 substantially equal in circumference to the circumference of catheter 22. FIG. 4B additionally shows that chamber 106 of second seal 98 has an inner surface 112. FIG. 4B shows an annular groove 114 is formed in inner surface 112 of second seal 98.

FIG. 4C shows that member 100 of rear connector 20 has a distal end 116 and a proximal end 118. FIG. 4C further shows member 100 is formed with a duct 120. FIG. 4C additionally shows that rear connector 20 includes a tubular extension 122, formed with a tubular passage 124, having a distal end 126 and a proximal end 128. FIG. 4C shows that proximal end 128 of tubular extension 122 is attached to distal end 116 of member 100. It is further shown in FIG. 4C that duct 120 is aligned with tubular passage 124. Further, it can be seen in FIG. 4C that an annular collar 130 extends radially from distal end 126 of tubular extension 122 an annular distance 132. As can be appreciated by cross-reference between FIGS. 4B and 4C, annular collar 130 on tubular extension 122 is snapably engageable with annular groove 114 in second seal 98.

As further shown in FIG. 4C, a second annular threaded surface 134 is formed in member 100 a threaded distance 136 from distal end 116 of member 100 for engaging first annular threaded surface 94 on seal expander 18.

To more clearly understand the operation of seal 52, reference first is made FIG. 4A. FIG. 4A shows that one or more bosses 138a and 138b are formed on outer surface 78 of first passageway 74 of insertion tube 66 for lockably engaging seal expander 18 with retaining ring 36 of housing 32 of introducer 16. Referring now to FIG. 3B, it will be seen that cutting tool 24 attached to distal end 26 of catheter 22 is enclosed within insertion tube 66. FIG. 3B also shows locking bosses 138a and 138b engaged with retaining ring 36. As can be appreciated with reference to FIG. 3B, by positioning cutting tool 24 within insertion tube 60 prior to parting expandable opening 54 with insertion tube 60, damage to seal 52 by cutting tool 24 is avoided. As further shown in FIG. 3B, as insertion tube 66 is inserted through expandable opening 54 created by the configuration of disks 58a, 58b, and 58c, disks 58a, 58b, and 58c part as shown in FIG. 3B. As also shown in FIG. 3B, after seal expander 18 is engaged with introducer 16, catheter 22 can be advanced through into lumen 30 of introducer 16 as shown in phantom in FIG. 3B without causing damage to seal 52. As shown in FIG. 5D, when insertion tube 66 is locked in introducer 16 as shown in FIG. 3B, circular hole 60 in first disk 58a expands to hug outer surface 78 of first passageway 74 of insertion tube 66. As further shown in FIG. 5E, first radial slit 62 in second disk 58b is parted to substantially hug outer surface 78 of first passageway 74 of insertion tube 66. As also shown in FIG. 5F, second radial slit 64 in third disk 58c is parted to substantially hug outer surface 78 of first passageway 74 of insertion tube 66. As can be appreciated by cross-reference among FIGS. 3B, 5D, 5E, and 5F, the configuration of disks 58a, 58b, and 58c form a fluid tight seal against fluid flow from lumen 30 during operation of rotatable atherectomy catheter 22.

Figure 5F:
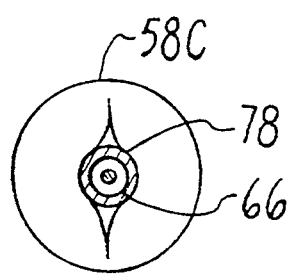

FIG. 4D shows seal expander 18 and rear connector 20 engaged during insertion of catheter 22 through device 10. FIG. 4D shows tapered angle 108 of second seal 98 compressed by beveled angle 90 of second passageway 84 of body 68. As will be appreciated by those skilled in the art, the compression of distal end 102 of second seal 98 causes orifice 110 to hug catheter 22, forming a fluid tight seal around rotating catheter 22 to prevent fluid leakage from device 10.

While the particular introducer sheath with seal protector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for introducing a rotatable atherectomy catheter into a vessel of a patient, which comprises:
   an elongated hollow sheath formed with a lumen, said sheath having a distal end, a proximal end, and having sufficient length for said proximal end to remain extracorporeal while said distal end is positioned in said vessel;
   a housing formed with a bore, said housing being attached to said proximal end of said sheath with said bore aligned in fluid communication with said lumen of said sheath;
   a first seal formed with an expandable opening, said seal being mounted in said bore of said housing to selectively prevent fluid flow through said seal;
   a seal expander engageable with said housing for expanding said opening for subsequent insertion of said catheter into said vessel of said patient through said device;

a substantially cylindrical insertion tube forming a first passageway through said seal expander, said insertion tube having a distal end and a proximal end, said proximal end of said insertion tube being attached to a substantially cylindrical body formed with a second passageway aligned with said first passageway, said second passageway having a distal end and a proximal end;

a bevel formed in said distal end of said second passageway;

a rear connector engageable with said seal expander for preventing fluid leakage from said device during operation of said rotatable atherectomy catheter.; and a substantially tube shaped second seal within said second passageway, said second seal having a distal end and a proximal end, said proximal end of said second seal being attached to said rear connector, and said distal end of said second seal being tapered;

wherein engagement of said rear connector with said seal expander urges said taper on said second seal against said bevel in said second passageway, compressing said distal end of said second seal to seal around said rotatable catheter.

2. A device as recited in claim 1, wherein said first seal includes a plurality of penetrable disks serially mounted in said bore.

3. A device as recited in claim 2, wherein said first seal includes a first disk formed with a circular hole through the center thereof, a third disk formed with a radial slit therethrough, and a second disk intermediate said first disk and said third disk, said second disk being formed with a radial slit therethrough, said slit of said second disk being aligned substantially at right angles to said slit of said third disk.

4. A device as recited in claim 3, further comprising a retaining ring attached to said housing at said proximal end of said bore for securing said first seal in said bore.

5. A device as recited in claim 1, wherein said rear connector comprises a substantially cylindrical member having a distal end and a proximal end, said member being formed with a duct through said member, said duct being aligned with said second passageway in said seal expander when said connector is engaged with said seal expander.

6. A device as recited in claim 5, wherein said rear connector further comprises a substantially cylindrical tubular extension having a tubular passage, said extension having a distal end and a proximal end, said proximal end of said extension being attached to said distal end of said member, said tubular passage being aligned with said duct in said member.

7. A device as recited in claim 5, further comprising means for connecting said expander with said connector.

8. A device for introducing a rotatable atherectomy catheter into the vessel of a patient which comprises:

introducer means having a lumen for establishing a fluid passageway extending from outside said patient into a vessel of said patient;

first sealing means attached to said introducer means mounted across said lumen for selectively blocking said fluid passageway;

penetrating means engageable with said introducer means for parting said first sealing means to unblock said fluid passageway for insertion of said catheter through said lumen into said vessel;

a beveled passageway formed in said penetrating means;

a connector engageable with said penetrating means; and tapered second sealing means within said beveled passageway;

wherein engagement of said connector with said penetrating means urges said tapered second sealing means against said beveled passageway, thereby compressing said second sealing means to seal around said catheter.

9. A device as recited in claim 8, wherein said introducer means for establishing a fluid passageway comprises an elongated hollow sheath, said sheath having a distal end, a proximal end, and having sufficient length for said proximal end to remain extracorporeal while said distal end is positioned in said artery.

10. A device as recited in claim 8, wherein said introducer means further comprises a housing formed with a bore, said housing being attached to said proximal end of said sheath with said bore aligned with said fluid passageway.

11. A device as recited in claim 8, wherein said first sealing means attached to said introducer means is a stratified seal formed with an expandable opening, said stratified seal being mounted in said bore of said housing to selectively prevent fluid flow through said stratified seal.

12. A device as recited in claim 11, wherein said stratified seal includes a plurality of penetrable disks serially mounted in said bore.

13. A device as recited in claim 12, wherein said stratified seal includes a first disk formed with a circular hole in the center of said first disk, a third disk formed with a radial slit therethrough, and a second disk intermediate said first disk and said third disk formed with a radial slit therethrough, said slit of said second disk being aligned substantially at right angles to said slit of said third disk.

14. A device as recited in claim 8, wherein said means engageable with said introducer means for penetrating said expandable means comprises a seal expander having a substantially cylindrical insertion tube forming a first passageway, said insertion tube having a distal end and a proximal end, said proximal end of said insertion tube being attached to a substantially cylindrical body formed with a second passageway aligned with said first passageway, said second passageway having a distal end and a proximal end.

15. A device as recited in claim 14, wherein said distal end of said second passageway is beveled to form a circular opening between said first passageway and said second passageway.

16. A device as recited in claim 8, wherein said connector has a substantially cylindrical tubular extension having a tubular passage, said extension having a distal end and a proximal.

17. A device as recited in claim 16, wherein said second sealing means comprises a substantially tube shaped second seal forming a chamber, having a distal end and a proximal end, said proximal end of said second seal being attached to said distal end of said tubular extension, and said distal end of said second seal being tapered to form an orifice at said distal end of said second seal.

18. A device as recited in claim 17, further comprising means for connecting said penetrating means with said connector.

* * * * *